United States Patent
Aichinger et al.

(10) Patent No.: US 6,177,590 B1
(45) Date of Patent: *Jan. 23, 2001

(54) METHOD FOR THE PRODUCTION OF (METH)ACRYLIC ACID ESTERS

(75) Inventors: Heinrich Aichinger, Mannheim; Michael Fried, Heidelberg; Gerhard Nestler, Ludwigshafen; Albrecht Dams, Wachenheim, all of (DE)

(73) Assignee: BASF Aktiengesellschaft, Ludwigshafen (DE)

( * ) Notice: Under 35 U.S.C. 154(b), the term of this patent shall be extended for 0 days.

This patent is subject to a terminal disclaimer.

(21) Appl. No.: 09/308,253

(22) PCT Filed: Nov. 21, 1997

(86) PCT No.: PCT/EP97/06514

§ 371 Date: May 25, 1999

§ 102(e) Date: May 25, 1999

(87) PCT Pub. No.: WO98/23577

PCT Pub. Date: Jun. 4, 1998

(30) Foreign Application Priority Data

Nov. 25, 1996 (DE) .............................................. 196 48 745

(51) Int. Cl.⁷ .......................... C07C 67/08; C07C 67/58; C07C 69/54
(52) U.S. Cl. ........................................... 560/205; 560/218
(58) Field of Search ...................................... 560/205, 218

(56) References Cited

U.S. PATENT DOCUMENTS 4,280,010 * 7/1981 Erpenbach et al. ..
5,093,520 * 3/1992 Nestler et al. ..
5,386,052  1/1995 Sakakura et al. ..................... 560/205
5,510,514  4/1996 Fauconet et al. ..................... 560/218

FOREIGN PATENT DOCUMENTS 0 566 074 10/1993 (EP) .
0 618 187  1/1995 (EP) .
0 609 127  4/1996 (EP) .

OTHER PUBLICATIONS

Chemical Abstracts, vol. 92, p. 566, AN 92:163,589n, CZ 179,808, Jul. 15, 1979.

Kirk–Othmer, Encycl. Of Chem. Technol., vol. 1, pp. 347–348, "Acrylic Acid and Derivatives".

\* cited by examiner

Primary Examiner—Gary Geist
Assistant Examiner—Leigh C. Maier
(74) Attorney, Agent, or Firm—Oblon, Spivak, McClelland, Maier & Neustadt, P.C.

(57) ABSTRACT

A process is described for preparing (meth)acrylic esters by reacting (meth)acrylic acid with $C_4$–$C_{12}$-alkanols in the presence of sulfuric acid or a mono-$C_4$–$C_{12}$-alkyl sulfate as catalyst, where the catalyst is regenerated by extraction with water from the reaction mixture and the aqueous catalyst solution is recycled back to the esterification, the concentration of unreacted alkanol in the reaction mixture to be extracted being not more than 5% by weight, based on the reaction mixture to be extracted.

13 Claims, No Drawings

METHOD FOR THE PRODUCTION OF (METH)ACRYLIC ACID ESTERS

The invention relates to a process for preparing esters of acrylic acid or methacrylic acid [(meth)acrylic acid].

(Meth)acrylic esters are generally prepared industrially by esterifying (meth)acrylic acid with alkanols in the presence of strong acids as esterification catalysts (eg. a mineral acid, such as sulfuric acid or phosphoric acid, alkanesulfonic acids or arylsulfonic acids). Processes of this type are disclosed, for example, by Kirk Othmer, "Encyclopedia of Chemical Technology", Vol. 1, pp. 347–348. The content of catalysts in the esterification mixture can vary in an order of magnitude from a tenth of a percent to several percent. When polybasic mineral acids are used as catalyst, the mineral acid is readily esterified by the alkanol present, forming the monoester, which is the actual esterification catalyst. The reaction mixture contains a relatively large amount of this monoester when the esterification is completed.

The acids used as catalysts and their esters which may be formed must be eliminated from the reaction mixture prior to further processing. Generally, this is achieved by extracting and neutralizing the reaction mixture with alkali metal hydroxide solution and alkaline earth metal hydroxide solution or carbonate solutions. This operation produces wastewaters whose disposal is complex and environmentally polluting. If sulfuric acid is used as catalyst, as mentioned, the monoester of sulfuric acid with the alkanol in question is primarily formed. The salts of the sulfuric monoesters, in particular of the esters with higher alkanols, are surface-active and on their disposal they would considerably impair the quality of the wastewaters from the process and would cause a not insignificant loss of product of value. For economic and ecological reasons, recovery and recycling of the catalyst is thus desirable.

The prior art includes a plurality of processes, all of which are burdened with considerable disadvantages, however.

EP-A-0 609 127 describes a process for preparing (meth)acrylic esters, in which the alcohol component is recovered by acid hydrolysis from the corresponding sulfuric monoester which is formed from sulfuric acid and the alcohol during the esterification. This process is complex, environmentally polluting and uneconomic.

CZ-B-179 808 describes a process for recovering mineral acids from esterification mixtures by extracting the esterification mixture with water, concentrating the aqueous phase by distillation and recycling the concentrated aqueous catalyst solution thus obtained to the esterification reaction. This process is energy-consuming.

EP-A-0 618 187 (≙ U.S. Pat. No. 5,386,052) describes a process for preparing (meth)acrylic esters, in which the catalyst is extracted with water and the extract, with or without concentration by distillation, is recycled to the esterification reaction. However, it is particularly emphasized here that sulfuric acid, owing to the poor extractability of the monoalkyl sulfate, is unsuitable as a catalyst, because the large amount of water which would be necessary for adequate extraction of the monoalkyl sulfate would adversely affect the esterification reaction. As catalyst, therefore, use is made of alkylsulfonic or arylsulfonic acids (column 2, lines 55ff), which are considerably more expensive than sulfuric acid, however.

It is an object of the present invention to develop a technically simple and economic process for preparing (meth)acrylic esters which successfully uses sulfuric acid as esterification catalyst and which permits the esterification catalyst (sulfuric acid or monoalkyl sulfate) to be separated off very simply and substantially completely from the resulting reaction mixture. In addition, the catalyst shall be recyclable back to the esterification directly, ie. without additional concentration by distillation, without affecting the esterification.

It has surprisingly been found that the catalyst can be extracted from the reaction mixture (esterification mixture) if the content of alkanol in said mixture is not more than 5% by weight.

We have found that this object is achieved by a process for preparing (meth)acrylic esters by reacting (meth)acrylic acid with $C_4$–$C_{12}$-alkanols, preferably $C_4$–$C_{10}$-alkanols, particularly preferably $C_4$–$C_8$-alkanols, in the presence of sulfuric acid or a mono-$C_4$–$C_{12}$-alkyl sulfate as catalyst, which comprises regenerating the catalyst by extraction with water from the reaction mixture and recycling the aqueous catalyst solution back to the esterification, the concentration of unreacted alkanol in the reaction mixture to be extracted being not more than 5% by weight, based on the reaction mixture to be extracted.

It has surprisingly been found that the alkanol content has a great influence on the extractability of the monoalkyl sulfate, which is formed from sulfuric acid and alkanol and which acts as the actual esterification catalyst; surprisingly the catalyst can be extracted from the reaction mixture (esterification mixture) if the alkanol content in the mixture is not more than 5% by weight (see Table 1). As a result, the catalyst can be extracted with small amounts of water, so that the extract can be directly recycled back to the esterification. Preferably, a reaction mixture whose alkanol content is ≦3% by weight, and in particular ≦1% by weight, is extracted.

In order to achieve an alkanol content of not more than 5% by weight, preferably, a high degree of esterification is brought about, eg. by distilling off the reaction water; and/or a suitable ratio of starting materials is selected. If the residual alkanol content is then still more than 5% by weight, the alkanol is distilled off in a conventional distillation apparatus (eg. column equipped with sieve trays, Raschig rings, ordered packings etc.). Surprisingly, despite the presence of the strongly acid esterification catalyst, no acid-catalyzed side reactions, such as ether or olefin formation or addition of the alkanol to the double bond of the (meth)acrylate (Michael addition), may be observed here to any significant extent.

The distillation is carried out in a customary manner; the distillation conditions depend on the type of alkanol used.

The alkanol is preferably distilled off down to a residual alkanol content in the reaction mixture which enables the catalyst (sulfuric acid) to be extracted with water without problems. In particular, the residual alkanol content is ≦5% by weight, preferably ≦3% by weight, particularly preferably ≦1% by weight, based on the reaction mixture.

Preferably, the conditions for extracting the catalyst from the esterification mixture are selected in such a manner that the catalyst concentration (sulfuric acid and monoalkyl sulfate) in the aqueous phase is at least 20% by weight, in particular at least 25% by weight, based on the aqueous extract, and the degree of extraction is at least 70% by weight, in particular at least 80% by weight, based on the amount of catalyst in the reaction mixture. To achieve this, from about 5 to 20% by weight of water, in particular from about 8 to 15% by weight of water, based on the total weight of the esterification mixture, is used for the extraction. The resulting extract can be recycled, without concentrating it, back to the esterification.

The extraction can be carried out in a manner known per se. Preferably, extraction is performed in counter-current, eg. in columns having no energy input, pulsed columns, columns equipped with internals, mixer-settler apparatuses or in static mixers.

The extraction can be carried out at ambient temperature or above, but expediently in the range from about 15 to 40° C.

The esterification is essentially carried out in a conventional manner, ie. by reacting (meth)acrylic acid with a $C_4$–$C_{12}$-alkanol in the presence of a catalyst and at elevated temperature. The molar ratio of alkanol:acrylic acid or methacrylic acid is generally 1:0.8–1.2. $C_4$–$C_{12}$-Alkanols are, for example, pentanol, hexanol, heptanol, octanol, 2-ethylhexanol, nonanol, 2-propylheptanol, decanol, undecanol, dodecanol, and, preferably, butanols, in particular n-butanol. The sulfuric acid concentration in the reaction mixture is generally from 0.5 to 10% by weight, preferably from 1 to 5% by weight, based on the total batch.

As polymerization inhibitors, use is made of, for example, phenothiazine, hydroquinone, hydroquinone monomethyl ether, or mixtures of these with or without air (from 0.1 to 10 l/h×l) in an amount of 100 to 5000 ppm, based on the reaction mixture. As an entrainer for removing water from the reaction mixture, use can be made in the process according to the invention of saturated hydrocarbons (eg. cyclohexane) or aromatics (eg. toluene); preferably, the reaction is carried out without additional entrainer, however.

The reaction is generally carried out at from about 70 to 160° C., preferably at from 90 to 130° C.

The reaction time is generally from about 1 to 10, preferably from 1 to 6, hours.

The reaction can be carried out under atmospheric pressure, reduced pressure or superatmospheric pressure. Preferably, the pressure is set so that the water formed during the esterification distils off, for example in the form of a mixture of water, $C_4$–$C_{12}$-alkanol and ester (the organic components are fed back to the esterification in this case). The esterification can be carried out continuously or batchwise, the continuous procedure being preferred.

The esterification is carried out in conventional apparatuses, eg. in an esterification unit of one or more heatable stirred reactors (cascade), which may be equipped with columns, condensers and phase-separation vessels. The reactor contents are mixed by stirring or other customary and suitable measures.

If, after the extraction of the catalyst, a further extraction/neutralization of the residual acids (catalyst and (meth)acrylic acid) using an aqueous base is necessary, this can be performed in a conventional extraction apparatus (see above), the requirement of base being low owing to the high degree of extraction of the catalyst and the extraction surprisingly proceeding without the phase-separation problems described in EP-A-0 566 074.

The ester is isolated in a conventional manner, in particular by distillation, eg. by distillation in a sieve-tray column, from the reaction mixture which has been freed from catalyst and, if appropriate, residual carboxylic acid and low-boilers.

The Example below illustrates the invention, without restricting it. Percentages are by weight.

A stirred-tank cascade consisting of 3 stirred reactors, each of 1 l reaction volume, which are equipped with column, condenser and phase-separation vessel, was charged with 558 g of acrylic acid, 648 g of n-butanol, 16 g of sulfuric acid and 1 g of phenothiazine per hour. The reaction temperature in the reactors was 106° C., 118° C. and 123° C., respectively, and the pressure was 700 mbar. At the top of the column, a mixture of water, n-butanol and n-butyl acrylate was produced, which separated into an aqueous and an organic phase, the organic phase being fed as reflux to the column.

The reaction efflux (1070 g/h) contained, according to analysis:
90.2% n-butyl acrylate
2.7% n-butanol
0.5% acrylic acid
2.2% monobutyl sulfate
Remainder: byproducts, polymers, oligomers, phenothiazine
Acrylic acid turnover: 99%, conversion 98%

The reaction efflux cooled to 25° C. was extracted in a mixer-settler apparatus at approximately 25° C. with 90 g/h of water. The aqueous phase (97 g/h) contained 20.5% mono-n-butyl sulfate (85% recovery) and 0.5% sulfuric acid.

This aqueous phase was recycled to the lower part of the distillation column of the first reactor, with the addition of fresh sulfuric acid having been decreased to 1.3 g/h. The acrylic acid turnover was again 99%, the conversion 98%.

The relationship between the degree of extraction of the catalyst and the n-butanol content of the reaction mixture fed to the extraction was determined by extracting esterification mixtures, which had been prepared by esterifying acrylic acid with n-butanol in the presence of sulfuric acid, and which had different n-butanol contents, once in a separating funnel with 10% by weight of water at 25° C. The results of these experiments are shown in Table 1 and verify the importance of a reaction procedure which keeps the content of unreacted alkanol below 5%, preferably at from 0.1% to 3%.

TABLE 1

| n-Butanol content | 0.1% | 2.5% | 5.0% | 10% |
|---|---|---|---|---|
| Catalyst content | 1.93% | 1.88% | 1.83% | 1.75% |
| Degree of extraction | 89% | 88% | 71% | 55% |
| Residual catalyst content | 0.22% | 0.23% | 0.53% | 0.97% |

We claim:

1. A process for preparing (meth)acrylic esters by reacting (meth)acrylic acid with a $C_4$–$C_{12}$-alkanol in the presence of sulfuric acid or a mono-$C_4$–$C_{12}$-alkyl sulfate as catalyst, which comprises regenerating the catalyst by extraction with water from the reaction mixture, the concentration of unreacted alkanol in the reaction mixture to be extracted being not more than 3% by weight, based on the reaction mixture to be extracted, and
   wherein the aqueous solution of the catalyst regenerated by extraction with water from the reaction mixture is recycled back to the esterification.

2. A process as claimed in claim 1, wherein the unreacted alkanol concentration is from 0.1 to 3% by weight.

3. A process as claimed in claim 1, wherein the catalyst is extracted in such a manner that the degree of extraction is at least 70% by weight, based on the amount of catalyst in the reaction mixture.

4. A process as claimed in claim 1, wherein the catalyst is extracted in such a manner that the catalyst concentration in the water phase is at least 20% by weight, based on the aqueous extract.

5. A process as claimed in claim 1, wherein the extraction is performed at from 15 to 40° C.

6. A process as claimed in claim 1, wherein the extraction is carried out in counter-current or in a static mixer.

7. A process as claimed in claim 1, wherein the alkanol used is n-butanol or isobutanol.

8. A process as claimed in claim 1, wherein the reaction is performed at from 70 to 160° C.

9. A process as claimed in claim 1, wherein the reaction time is from 1 to 10 hours.

10. A process as claimed in claim 3, wherein the catalyst is extracted in such a manner that the degree of extraction is at least 80% by weight, based on the amount of catalyst in the reaction mixture.

11. A process as claimed in claim 4, wherein the catalyst is extracted in such a manner that the catalyst concentration in the water phase is at least 25% by weight, based on the aqueous extract.

12. A process as claimed in claim 8, wherein the reaction is performed at from 90 to 130° C.

13. A process as claimed in claim 9, wherein the reaction time is from 1 to 6 hours.

\* \* \* \* \*

UNITED STATES PATENT AND TRADEMARK OFFICE
CERTIFICATE OF CORRECTION

PATENT NO. : 6,177,590

DATED : January 23, 2001

INVENTOR(S): Heinrich AICHINGER, et al.

It is certified that an error appears in the above-identified patent and that said Letters Patent is hereby corrected as shown below:

On the title page, the CPA information has been omitted. It should read as follows:

---[ * ]  Notice:    This patent issued on a continued prosecution application filed under 37 CFR 1.53(d), and is subject to the twenty year patent term provisions of 35 U.S.C. 154(a)(2).   ---

Signed and Sealed this

Fifteenth Day of May, 2001

Attest:

NICHOLAS P. GODICI

Attesting Officer      Acting Director of the United States Patent and Trademark Office

UNITED STATES PATENT AND TRADEMARK OFFICE
CERTIFICATE OF CORRECTION

PATENT NO. : 6,177,590 B1
DATED : January 23, 2001
INVENTOR(S) : Heinrich Aichinger et al.

It is certified that error appears in the above-identified patent and that said Letters Patent is hereby corrected as shown below:

<u>Title page,</u>
Item [*] Notice, should read as follows -- This patent issued on a continued prosecution application filed under 37 CFR 1.53(d), and is subject to the twenty year patent term provisions of 35 U.S.C. 154(a)(2). --

Signed and Sealed this

Fifth Day of October, 2004

JON W. DUDAS
*Director of the United States Patent and Trademark Office*